(12) United States Patent
Daksis et al.

(10) Patent No.: US 6,645,733 B1
(45) Date of Patent: Nov. 11, 2003

(54) FLUORESCENT INTENSITY METHOD FOR ASSAYING BINDING BETWEEN PROTEINS OR PEPTIDES

(75) Inventors: Jasmine I. Daksis, Ontario (CA); Glen H. Erikson, Ontario (CA)

(73) Assignee: Ingeneus Corporation, Bridgetown (BB)

( * ) Notice: Subject to any disclaimer, the term of this patent is extended or adjusted under 35 U.S.C. 154(b) by 0 days.

(21) Appl. No.: 09/344,525

(22) Filed: Jun. 25, 1999

(51) Int. Cl.$^7$ .................. G01N 21/00; G01N 31/00; G01N 31/14
(52) U.S. Cl. ............. 435/7.92; 435/6; 435/7.1; 435/7.21; 435/7.81; 435/7.93; 435/810; 436/501; 436/536; 436/537; 436/172; 436/517; 436/545; 536/24.1; 536/24.3; 536/23.1; 536/23.31; 536/23.32
(58) Field of Search ................ 435/5, 6, 7.1, 7.21, 435/7.8, 7.93, 91.2, 810, 968, 7.92; 436/501, 536, 537, 800, 172, 545, 517, 546, 15, 34, 164, 171, 804; 536/24.1, 24.3, 23.1, 23.31, 23.32, 23.33, 25.3

(56) References Cited

U.S. PATENT DOCUMENTS

| | | |
|---|---|---|
| 4,207,075 A | 6/1980 | Liburdy |
| 4,220,450 A | 9/1980 | Maggio |
| 4,235,869 A * | 11/1980 | Schwarzberg .................. 424/8 |
| 4,743,535 A | 5/1988 | Carrico |
| 4,761,382 A | 8/1988 | Woodhead et al. |
| 4,963,477 A | 10/1990 | Tchen |
| 5,171,695 A * | 12/1992 | Ekins ......................... 436/501 |
| 5,187,106 A | 2/1993 | Fritzsche et al. |
| 5,217,866 A | 6/1993 | Summerton et al. |
| 5,332,659 A | 7/1994 | Kidwell |
| 5,334,537 A | 8/1994 | Lee et al. |
| 5,445,935 A | 8/1995 | Royer |
| 5,503,980 A | 4/1996 | Cantor |
| 5,516,635 A * | 5/1996 | Ekins et al. .................. 435/6 |
| 5,538,848 A | 7/1996 | Livak et al. |
| 5,539,082 A | 7/1996 | Nielsen et al. |
| 5,594,138 A | 1/1997 | Dykstra et al. |
| 5,674,698 A | 10/1997 | Zarling et al. |
| 5,747,247 A | 5/1998 | Kowalczykowski et al. |
| 5,756,292 A | 5/1998 | Royer |
| 5,783,384 A | 7/1998 | Verdine |
| 5,814,468 A * | 9/1998 | Siiman et al. ............... 435/7.2 |
| 5,846,729 A | 12/1998 | Wu et al. |
| 6,297,059 B1 * | 10/2001 | Song et al. .................. 436/501 |

FOREIGN PATENT DOCUMENTS

| | | |
|---|---|---|
| EP | 0 232 967 | 8/1987 |
| EP | 0 512334 | 11/1992 |
| EP | 0 599337 | 6/1994 |
| WO | WO 87/07955 | 12/1987 |
| WO | 92 18650 | 10/1992 |
| WO | 93 24652 | 12/1993 |
| WO | 94 12665 | 6/1994 |
| WO | WO 94/14980 A1 | 7/1994 |
| WO | 94 25477 | 11/1994 |
| WO | WO 95/15981 | 6/1995 |
| WO | 96 34983 | 11/1996 |
| WO | 97 12995 | 4/1997 |
| WO | WO 98/04923 A1 | 2/1998 |
| WO | WO 98/26093 A2 | 6/1998 |

OTHER PUBLICATIONS

Shearer et al., "Heterogeneity of IgG Determined by Fluorescence" in *Biochemical Fluorescence: Concepts,* vol. 2, (Chen et al., Eds. 1976), pp. 811–843.

Kadonaga et al., "Isolation of cDNA Encoding Transcription Factor Sp1 and Functional Analysis of the DNA Binding Domain," Cell, 51:1079–1090, Dec. 24, 1987.

Lansdorp, "Close Encounters of the PNA Kind," 14 Nature Biotechnology 1653 (Dec. 1996).

Matthews et al., "Analytical Strategies for the Use of DNA Probes," 169 Analytical Biochemistry 1 (1988).

Motulsky, "The GraphPad Guide to Analyzing Radioligand Binding Data," pp. 1–19, 1995–96.

Perry–O'Keefe et al., "Peptide Nucleic Acid Pre–Gel Hybridization: An Alternative to Southern Hybridization," 93 Proc. Natl. Acad. Sci. USA 14670 (Dec. 1996).

"PNA Oligomers as Hybridization Probes," vol. 1, Issue 2 of PerSeptive Biosystems Magazine.

Rawls, "Optimistic About antisense," 75(22) Chem. Eng. News 35, 39 (Jun. 2, 1997).

Smulevitch et al., "Enhancement of Strand Invasion by Oligonucleotides Through Manipulation of Backbone Charge," 14 Nature Biotechnology 1700 (Dec. 1996) (disclosed in Landsdorp, "Close Encounters of the PNA Kind," 14 Nature Biotechnology 1653 (Dec. 1996).

(List continued on next page.)

*Primary Examiner*—Long V. Le
*Assistant Examiner*—Changhwa J Cheu
(74) *Attorney, Agent, or Firm*—Caesar, Rivise, Bernstein, Cohen & Pokotilow, Ltd.

(57) ABSTRACT

A method for assaying specific binding between a fluorophore-labeled probe and an unlabeled target is provided. The method includes detecting a quenching effect on fluorescence emitted by the fluorophore-labeled probe resulting from binding. The method is conducted without separating complexes of the target and probe from the free target and free probe prior to quenching effect detecting, and without providing a signal quenching agent to quench fluorescent light. Preferably, the probe and target are amino acid-containing compounds, such as proteins. The method can be used for a variety of applications, including screening for drug candidates having optimum binding properties, and quantifying and classifying the binding characteristics between peptide-containing compounds. The method is more sensitive than conventional assays, enabling the analysis of minute samples and low affinity binding interactions between receptors and ligands that are below the detection limits of conventional technology.

22 Claims, 2 Drawing Sheets

OTHER PUBLICATIONS

Sturm et al., "The ubiquitous octamer–binding protein Oct.–1 contains a POU domain with a homeo box subdomain," Genes & Development, 2:1582–1599, 1988.

Tomac et al., "Ionic Effects on the Stability and Conformation of Peptide Nucleic Acid Complexes," 118 J.Am.Chem. Soc. 5544 (1996).

Uhlmann et al., Chemical Reviews, vol. 90, No. 4, pp. 543–584. 1990.

Wilson et al., "The VP16 Accessory Protein HCF Is a Family of Polypeptides Processed from a Large Precursor Protein," Cell, 74:115–125, Jul. 16, 1993.

Cardullo et al, "Detection of nucleic acid hydridization by nonradiative fluorescence resonance energy transfer," 85(23) PNAS USA 8790 (1988).

Coghlan, "One–step DNA test in a tube," New Scientist, Technology, p. 21, Nov. 5, 1994.

Cooper et al., "Analysis of fluorescent energy transfer in duplex and branched DNA molecules," 29 Biochemistry 9261 (1990).

Dalrymple et al., "DNA sequence of the herpes simplex virus type 1 gene whose product is responsible for transciptional activation of immediate early promoters," Nucleic Acids Research, vol. 13, No. 21, pp. 7865–7879, 1985.

Egholm et al., "PNA Hybridizes to Complementary Oligonucleotides Obeying the Watson–Crick Hydrogen–Bonding Rules," 365 Nature 566 (1993).

Heppell–Parton, "Gene Mapping by Fluorescence in Situ Hybridization," p. 350–54, in Molecular Biology and Biotechnology: A Comprehensive Desk Reference (Myers, ed. 1995).

Hill et al., "Fluorescence Approaches to Study of Protein–Nucleic Acid Complexation," Methods in Enzymology, 278:390–416, 1997.

Jensen et al., "Kinetics for Hybridization of Peptide Nucleic Acids (PNA) with DNA and RNA Studied with the BIAcore Technique," 36(16) Biochem. 5072 (Apr. 1997).

Bohmann et al., "Human Proto–Oncongen c–jun Encodes a DNA Binding Protein with Structural and Functional Properties of Transcription Factor AP–1," Science, 238:1386–1392, Dec. 1987.

Brown et al., "Fluorescence spectroscopy as a tool to investigate protein interactions," Current Opinion in Biotechnology, 1997, 8:45–49.

C. Garisson et al., "Screening for genetic mutations," 380 Nature 207 (Mar. 21, 1996).

EFTINK, "Fluorescence Techniques for Studying Protein Structure," 35 Methods of Biochemical Analysis 127–206 (1991).

Holbrook et al., "Malate Dehydrogenase. X. Fluorescence Microtitration Studies of D–Malate Hydroxymalonate, Nicotinamide Dinucleotide, and Dihdyronicotinamide–Adenine Dinucleotide Binding by Mitochondrial and Supernatant Porcine Heart Enzymes," 11(13) Biochemistry 2499–2502 (1972).

* cited by examiner

FIG. 1A. 10 nM Flu-angiotensin II:wildtype AT1 receptor binding

FIG. 1B. 10 nM mutant Flu-angiotensin II:wildtype AT1 receptor binding

FIG. 2A. Displacement of Flu-AII bound to AT1 receptors by AII

- 300 µM AII
- 0 units AT1
- 100 µM AII
- 3 µM AII
- 300 nM AII
- 10 nM AII
- 1 nM AII
- 0 nM AII

FIG. 2B. Displacement of Flu-AII bound to AT1 receptors by AII

FLUORESCENT INTENSITY METHOD FOR ASSAYING BINDING BETWEEN PROTEINS OR PEPTIDES

FIELD OF THE INVENTION

This invention relates to fluorescent intensity based methods for assaying binding between ligands and receptors, particularly ligands and receptors comprising amino acids and/or amino acid analogs.

BACKGROUND OF THE INVENTION

A detection method typically employs at least one analytical reagent that binds to a specific target macromolecular species and produces a detectable signal. These analytical reagents typically have two components: (1) a probe macromolecule, for example, an antibody or oligonucleotide, that can bind a target macromolecule with a high degree of specificity and affinity, and (2) a detectable label, such as a radioisotope or covalently-linked fluorescent dye molecule. In general, the binding properties of the probe macromolecule define the specificity of the detection method, and the detectability of the associated label determines the sensitivity of the detection method. The sensitivity of detection is in turn related to both the type of label employed and the quality and type of equipment available to detect it.

For example, radioimmunoassays have been among the most sensitive and specific analytical methods used for detecting and quantitating biological macromolecules. Radioimmunoassay techniques have been used to detect and measure minute quantities of specific analytes, such as polypeptides, drugs, steroid hormones, polynucleotides, metabolites, and tumor markers, in biological samples. Radioimmunoassay methods employ immunoglobulins labeled with one or more radioisotopes as the analytical reagent. Radiation (alpha, beta or gamma) produced by decay of the attached radioisotope label serves as the signal which can be detected and quantitated by various radiometric methods.

Radioisotope based assays used to measure peptide-protein, ligand-receptor or drug-receptor interactions have typically required one component (usually the peptide, ligand or drug) to be radioactively labeled with either $^{125}I$, $^{35}S$, $^{32}P$ or $^{3}H$ for detection and quantitation. Radioactive labeling is labor-intensive, time-consuming, a health and environmental hazard during synthesis, purification, storage, usage and disposal steps, and is relatively expensive. Radioligands or radioactively labeled peptides are most commonly labeled with $^{125}I$, which emits mainly γ radiation and some β radiation, and has a half-life of sixty days. $^{125}I$ is considered more dangerous than the other above-mentioned radioisotopes, due to its high volatility and the fact that it concentrates in the thyroid, thereby requiring more precautions and expense during its handling.

Conventionally, it has been necessary to separate interacting complexes from unbound radioactive probes either by filtration and extensive washing steps or by native polyacrylamide gel electrophoresis, followed by gel drying. Low affinity binding interactions may dissociate during extensive washing steps or migration through a gel, and thus not be detected. Dried gels are analyzed by autoradiography or phosphoimaging, which is very time-consuming, especially when $^{35}S$ or $^{3}H$ isotopes are used. Filtered $^{125}I$-bound complexes are analyzed by scintillation counting in special γ radiation scintillation counters.

Moreover, the sensitivity of traditional detection methods, such as radioimmunoassays, can be too low to detect particularly small or dilute samples.

Thus, a need has existed in the art for a simple, highly sensitive, effective and rapid method for analyzing interaction between ligands and receptors, particularly ligands and receptors comprising amino acids and/or amino acid analogs.

All references cited herein are incorporated herein by reference in their entireties.

SUMMARY OF THE INVENTION

The invention provides a method for assaying binding between at least one target and at least one probe, said method comprising:

providing at least one target comprising a peptide sequence or a peptide analog sequence;

providing at least one probe comprising an amino acid or a second amino acid analog, and at least one fluorophore;

providing a test medium comprising said at least one target and said at least one probe;

irradiating said test medium with radiation effective to cause said at least one fluorophore to emit fluorescent light; and detecting a quenching effect on fluorescence emitted by said at least one fluorophore resulting from said binding, wherein said binding is specific, and wherein said method is conducted without separating complexes of said at least one target and said at least one probe from free target and free probe prior to said quenching effect detecting, and without providing a signal quenching agent to quench said emitted fluorescence.

BRIEF DESCRIPTION OF THE DRAWINGS

The invention will be described in conjunction with the following drawings in which like reference numerals designate like elements and wherein:

FIGS. 1A, 1B and 2A are fluorescent spectra; and

FIG. 2B is a graph of percent specific binding of Flu-AII bound to AT1 receptor versus the log concentration of unlabeled AII added as competitor.

DETAILED DESCRIPTION OF PREFERRED EMBODIMENTS

The invention provides a rapid, sensitive, environmentally friendly, and safe method for assaying binding between a target and a probe, wherein the target comprises a peptide sequence or a peptide analog sequence and the probe comprises amino acid-containing or amino acid analog-containing compounds. It is preferred that the probe comprise a fluorescent label, but in alternative embodiments, the target instead of the probe can be so labeled. The preferred method of the invention comprises detecting a fluorescent intensity quenching effect on the fluorescent label resulting from specific binding between the target and probe.

The quenching effect detected in the method of the invention is a decrease in fluorescent intensity which is a direct indication of the percentage of specific binding between the target and the probe, such that a plot of the percentage specific binding as a function of the log concentration of fluorescent probe yields a classical sigmoidal dose-response curve. The instant method does not require the measurement of the polarization of fluorescence, unlike fluorescent anisotropy methods.

The target preferably comprises a peptide sequence or a peptide-like analog sequence, such as, e.g., a dipeptide, tripeptide, polypeptide, protein or a multi-protein complex. More preferably, the target is a protein having at least one receptor site for the probe.

The probe preferably comprises an amino acid or amino acid analog. For example, suitable probes can comprise a single amino acid, single amino acid analog, a peptide-like analog, peptidoid, peptidomimetic, peptide, dipeptide, tripeptide, polypeptide, protein or a multi-protein complex.

A variety of binding complexes can be assayed with the method of the invention. In embodiments, the invention is used to analyze binding characteristics (including the presence or absence of binding, and the binding affinity) between proteins and other amino acid based or amino acid analog based compounds. Suitable proteins for analysis include, e.g., wild-type, mutant, isolated, in vitro translated, and/or synthesized. The invention is particularly suitable for analyzing binding of ligands to protein receptors. Test samples need not be 100% pure, but rather, can comprise, e.g., a purified preparation, a synthesized preparation, a semi-purified protein extract, a crude protein extract, an in vitro translated preparation, a membrane preparation, whole cells or tissues.

The invention enables detecting the binding of a first unlabeled compound (e.g., a target) to a second unlabeled compound by detecting a change in the binding characteristics (as indicated by a change in the fluorescent intensity) between the first unlabeled compound and a labeled compound (e.g., a probe). For purposes of this invention, such detection is referred to as "secondary binding" detection, or in its broader sense, "indirect binding" detection. In theory, the invention enables tertiary binding detection, quaternary binding detection, and so forth, provided that each additional level of binding produces a significant change in binding between the labeled compound and the first unlabeled compound, or sufficiently alters the total mass of unlabeled compounds bound to the labeled compound.

Similarly, the invention also enables detecting the binding of an unlabeled compound to at least one member of a complex of complexed compounds, wherein at least one of the complexed compounds is labeled for fluorescent intensity measurements. The labeled compound and the unlabeled compound need not even directly interact for detection to occur. The essential point is that the invention enables detecting a condition through its indirect or direct influence on the binding characteristics of a labeled probe to a target.

Thus, the invention enables detecting the binding of an antibody (i.e., the "second unlabeled compound") to a specific protein (i.e., the "first unlabeled compound") against which the antibody is directed, wherein the specific protein is either directly bound to the labeled protein probe, or is present in a multi-protein complex and thus interacting with one or more other proteins in the complex, but not necessarily directly interacting with the labeled probe.

The invention further enables detecting direct and indirect binding of a labeled probe to other sequence-specific binding molecules, such as peptides, peptidomimetics, complex carbohydrates or other oligomers (detection of protein-DNA binding is disclosed in our copending U.S. patent application Ser. No. 09/224,505). In addition, the invention allows the detection of direct and indirect binding of a labeled sequence specific binding molecule, such as a peptide, peptide-like analog, peptidomimetic, complex carbohydrate or other oligomer, to at least one unlabeled protein.

The invention is useful for a vast number of purposes, including designing and/or selecting molecules that bind in a site-specific manner to a predetermined target, or that alter binding of other molecules to the target. The invention thus provides a method for identifying and evaluating new substances, or drugs, that have a specific binding activity, or that predictably alter the binding characteristics of other binding pairs/complexes.

The method of the invention can be conducted without separating the probe-target complex from the free probe and target prior to the fluorescent intensity detecting, and without providing a signal quenching agent on the probe or target.

The method does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

The method of the invention does not require a gel separation step, thereby allowing double the amount of samples to be tested and analyzed in just half a day. Quantitative analyses are simple and accurate.

The method of the invention is preferably conducted in a homogeneous solution, eliminating the requirement for separation of bound complexes from unbound probes, by either filtration and numerous washing steps or by gel electrophoresis. Consequently the binding assay saves a lot of time and expense, and can be easily automated. Furthermore, it enables binding variables such as buffer, pH, ionic concentration, temperature, incubation time and possible cofactor requirements to be rapidly determined. Since equilibrium interactions are not perturbed by additional steps that could cause dissociation, more accurate measurement of the equilibrium dissociation constant, $K_d$, of the binding molecule to the binding sites is possible. Moreover, analyses of low affinity binding interactions, that conventionally would go undetected, are now feasible.

The method significantly improves upon the sensitivity of prior art assays. The method of the invention is sufficiently sensitive to detect bound target at a concentration less than $1.5 \times 10^{-11}$ M, more preferably $1.0 \times 10^{-11}$ M or less. In embodiments, the method is sufficiently sensitive to detect bound target at a concentration of $3.0 \times 10^{-14}$ M to $1.0 \times 10^{-11}$ M. It should go without saying that the foregoing values are not intended to suggest that the method cannot detect higher concentrations.

In addition, the specificity of the binding interaction can be quickly assessed by the method of the invention by saturation binding experiments or competitive binding experiments. Saturation levels of binding are achieved when specific binding occurs, whereas non-specific binding, caused by the "stickiness" of a ligand to purified receptor preparations, membrane preparations, whole cells or tissues, is non-saturable, since no specific number of receptor sites are involved. Competitive binding experiments, where various concentrations of unlabeled ligands are tested for their ability to compete with a fixed concentration of a fluorescently-labeled ligand for receptor or protein binding, verify the specificity of the binding molecules as well as the quality of the binding sites.

The invention enables the elucidation of the number of binding sites in a particular protein preparation, and their affinity and accessibility for various drugs. A saturation binding experiment allows the determination of the equilibrium dissociation constant ($K_d$), defined as the concentration of ligand which occupies half of the receptors at equilibrium. A small $K_d$ indicates that the receptor has a high affinity for the ligand. Conversely, a large $K_d$ is indicative of a low affinity interaction. Knowing the concentration of ligand used in an experiment and its $K_d$ for any given receptor preparation, one can calculate the fractional occupancy, i.e., the fraction of all receptors that are bound to the ligand. Homologous competitive binding experiments, where the unlabeled and labeled ligands are the same compound, can also be used to determine the affinity of a ligand for the receptor and the receptor number.

The method of the invention is particularly advantageous for heterologous competitive binding experiments, where the unlabeled and labeled ligands are different compounds. Literally thousands of potential drugs can be screened quickly, efficiently and cheaply for binding ability to specific receptors by this assay. In this case, the putative drugs would be unlabeled. Furthermore, drugs could be identified as agonists, competitive antagonists or non-competitive antagonists. This assay is especially useful to study the interaction of low affinity drugs with receptors.

Competitive binding assays allow the determination of $IC_{50}$, the concentration of unlabeled ligand required to prevent 50% of the specific binding of the labeled ligand to the receptor. Knowing the $K_d$ and concentration of the labeled ligand, and the $IC_{50}$ of the unlabeled compound, one can then calculate the $K_i$, the equilibrium dissociation constant for binding of the unlabeled ligand or drug to the receptor and thus assess its binding affinity.

The invention further enables detecting the presence of more than one class of binding site within a given receptor preparation. For example, a protein membrane preparation derived from a tissue may contain two subtypes of a receptor with different binding affinities for a given ligand. Competitive binding experiments with such a receptor preparation may result in an extended range of unlabeled ligand concentrations required to displace the labeled ligand bound to the receptor preparation. In unusual cases where the two receptors exhibit extremely different binding affinities, a biphasic competitive binding curve may be observed, when the percent specific binding of the labeled ligand to the receptor is plotted against a log scale of the concentration of unlabeled ligand added.

The invention will be illustrated in more detail with reference to the following Examples, but it should be understood that the present invention is not deemed to be limited thereto.

EXAMPLES

Examples 1 and 2 demonstrate the specific binding of a fluorescently-labeled peptide to a single protein or multi-protein complex.

Example 1

The angiotensin system is a key regulator of blood pressure, plasma volume, water and electrolyte balance, and neuronal function in humans. The octapeptide angiotensin II (AII) hormone binds to and activates two G protein-coupled receptors, the angiotensin II AT1 and AT2 receptors, found in the cytoplasmic membrane of various cells such as vascular smooth muscle cells and adrenal gland cells. The AT1 receptors are responsible for most of the AII physiological actions.

Both AT1 and AT2 receptors possess a seven hydrophobic transmembrane domain structure, which is classical for G protein-coupled receptors. Binding by the 8 amino acid AII ligand involves amino acid residues on the top of several transmembrane domains and in extracellular loops of the receptor. It is hypothesized that AII binding induces changes in the receptor conformation by the rotation of transmembrane helices as the initial event for the subsequent activation of a G protein.

When AII binds to the AT1 receptor, it couples to various intracellular GTP-binding proteins (G proteins), namely the Gq/11 proteins. Coupling to the Gq/11 proteins activates several signaling pathways of the cell. The cloned human AT1 receptor (from NEN Life Science Products Inc., Boston, Mass.) used in the examples is a purified membrane preparation derived from Chinese hamster ovary (CHO) cells. This receptor preparation possesses both high and low affinity AII binding sites. The high affinity binding sites are coupled to the Gq proteins naturally present in CHO cells, while the low affinity binding sites are uncoupled to the G proteins. The human AT1 receptor is 359 amino acids or 41 KDa in size. The Gq proteins in CHO cells consist of αGq (42 KDa), βGq (40 KDa) and γGq (8 KDa).

Wildtype AII labeled with fluorescein at its amino-terminal end (Flu-AII), was synthesized by Advanced Bioconcept (Montreal, Canada), purified to >95% homogeneity by HPLC and verified by mass spectroscopy. 2.0 nmole of Flu-AII was reconstituted in 10 μl DMSO and resuspended in ddH$_2$O at a final concentration of 20 μM. The sequence for wildtype Flu-AII is as follows (SEQ ID NO:1):

Flu-Asp-Arg-Val-Tyr-Ile-His-Pro-Phe

Mutagenesis studies to define the minimal receptor domain of AII required for physiological binding and activation of AT1 revealed a minimal requirement for 6 amino acids. Except for phenylalanine, which is crucial at the C-terminus for activating the receptor, chain length is a more important factor for binding than the exact nature of the amino acid residues of the AII fragments. A mutant AII fragment containing the first five amino acid residues of wildtype AII and labeled with fluorescein at its amino-terminus [Flu-AII(1–5)] was synthesized by AnaSpec Inc. (San Jose, Calif.), purified to >95% homogeneity by HPLC and confirmed by mass spectroscopy. 4.9 μmole of Flu-AII (1–5) was dissolved in DMSO and resuspended in ddH$_2$O at a final concentration of 200 μM. The sequence for mutant Flu-AII(1–5) is as follows (SEQ ID NO:2):

Flu-Asp-Arg-Val-Tyr-Ile

The Flu-AII:AT1 binding reaction mixture (30 μl) contained the following: 40 mM Tris-HCl, pH 7.5, 5 mM MgCl$_2$, 1 mM EDTA, 0.25 mM PMSF, 0.0005 to 0.1 units of human AT1 receptor and 10 nM wildtype or mutant Flu-AII. The reaction mixtures were incubated at 37° C. for 1 hour, placed into a quartz cuvette, irradiated with an argon ion laser beam having a wavelength of 488 nm and monitored for fluorescent emission.

The fluorescence spectra obtained for the binding of 0.005 units to 0.05 units of AT1 receptor to 10 nM wildtype Flu-AII or 10 nM mutant Flu-AII(1–5) are illustrated in FIGS. 1A and 1B, respectively. The maximum fluorescent intensity occurred at 528 nm, since the fluorophore used was fluorescein. 0.005 units, 0.01 units, 0.02 units and 0.05 units of AT1 receptor reacted with 10 nM wildtype Flu-AII resulted in a 42%, 54%, 69% and 83% decrease in fluorescent intensity, respectively, compared to the intensity emitted by Flu-AII alone (FIG. 1A), indicative of binding. As the AT1 concentration was increased, progressively more binding to Flu-AII was observed, clearly demonstrating the quantitative nature of the fluorescently-labeled peptide to protein binding assay. The binding was specific as evidenced by the achievement of saturation levels of binding with 0.05 units of AT1 receptor. Non-specific binding, by definition, would be non-saturable, since no specific number of receptor sites would be involved.

Furthermore, the ligand to receptor binding assay is highly sensitive, resulting in a 42% and 83% decrease in fluorescent intensity when just 0.005 units and 0.05 units of AT1 receptor were bound to 10 nM wildtype Flu-AII (FIG. 1A). Even binding to AT1 receptor levels as low as 0.0005 units were detected, yielding an 18% decrease in fluorescent intensity when reacted with 10 nM Flu-AII (data not shown). By contrast, conventional binding assays using $^{125}$I-labeled AII, followed by filtration over glass fiber filters, require 1 unit of this AT1 receptor membrane preparation to be used. Therefore, the assay of the invention is at least 2000-fold more sensitive than the traditional $^{125}$I-ligand:receptor binding assay.

FIG. 1B illustrates that 0.005 units, 0.01 units, 0.02 units and 0.05 units of AT1 receptor did not bind with 10 nM mutant Flu-AII(1–5), resulting in minor increases in fluorescent intensity above that observed with mutant Flu-AII alone, confirming the specificity of the assay of the invention.

Example 2

The specificity of the assay of the invention was further verified by a competition binding experiment, where specific and non-specific competitors were tested for their ability to displace the binding of wildtype Flu-AII ligand to the cloned human AT1 receptor (as used in Example 1). Unlabeled human angiotensin II (specific competitor) and unlabeled human substance P (non-specific competitor) were obtained from Advanced Bioconcept (Montreal, Canada). Substance P is an eleven amino acid neuropeptide with numerous physiological activities, including the excitation of central and peripheral nerves, thereby regulating pain transmission and perception. Substance P binds specifically to the G protein-coupled receptor, neurokinin 1, and to a lesser extent to neurokinin 2, but is incapable of binding to the angiotensin II receptors.

100 nmole of AII and 100 nmole of substance P were reconstituted in 5 μl DMSO and resuspended in ddH$_2$O at a final concentration of 1 mM each. The sequence for wildtype AII is shown above (SEQ ID NO:1) with a fluorescein label.

The sequence for wildtype substance P is as follows (SEQ ID NO:3):

Met-Leu-Gly-Phe-Phe-Gln-Gln-Pro-Lys-Pro-Arg

The Flu-AII:AT1 binding reaction mixture (30 μl) contained the following: 40 mM Tris-HCl, pH 7.5, 5 mM MgCl$_2$, 1 mM EDTA, 0.25 mM PMSF, 0.02 units of human AT1 receptor and 10 nNM wildtype Flu-AII. Following a 15 minute incubation at 37° C, 1 nM, 3 nM, 10 nM, 30 nM, 100 nM, 300 nM, 1 μM, 3 μM, 10 μM, 30 μM, 100 μM and 300 μM of either unlabeled AII or unlabeled substance P were added to the reaction mixtures and incubated for an additional 1 hour at 37° C. The samples were then placed into a quartz cuvette, irradiated with an argon ion laser beam having a wavelength of 488 nm and monitored for fluorescent emission.

When 0.02 units of AT1 receptor were bound to 10 nM wildtype Flu-AII in the absence of unlabeled ligand, a 69% decrease in fluorescent intensity was observed, compared to the level achieved with Flu-AII alone (FIG. 2A). Addition of 1 nM, 10 nM, 300 nM, 3 μM and 100 μM of unlabeled AII to 10 nM Flu-AII bound to 0.02 units of AT1 receptor, resulted in a 65%, 58%, 43%, 35% and 14% decrease in fluorescent intensity, respectively, compared to the intensity emitted by Flu-AII alone (FIG. 2A). As the amount of unlabeled AII was increased, it competed with and displaced the Flu-AII bound to AT 1, resulting in progressively less quenches of fluorescent intensity, with a rate dependent on the equilibrium dissociation constant ($K_d$) of Flu-AII. Addition of 300 μM unlabeled AII (a 3×10$^4$-fold excess compared to the amount of Flu-AII) was able to fully compete with Flu-AII for AT1 receptor binding, resulting in no decrease in fluorescent intensity (FIG. 2A). This competition binding experiment confirmed that the Flu-AII was binding specifically to the AT1 receptor, and not merely sticking to the membrane preparation.

When the fluorescent intensity data from the above experiment was plotted as percent specific binding of Flu-AII bound to AT 1 receptor versus the log concentration of unlabeled AII added as competitor (FIG. 2B), a classical competitive binding curve was observed. The data were normalized from 100% specific binding (when no unlabeled AII was added) to 0% binding (when no AT1 receptor was present), as by convention. The IC$_{50}$, the concentration of unlabeled AII required to block 50% of the Flu-AII binding to the AT1 receptor can now be determined. Knowing the affinity of the Flu-peptide for the receptor ($K_d$), and the IC$_{50}$ of the unlabeled ligand, one can then calculate the K$_i$, the equilibrium dissociation constant for binding of the unlabeled ligand for the receptor, based on the following equation:

$$K_i = \frac{IC_{50}}{1 + \frac{[Labeled\ Ligand]}{K_d}}$$

The observation that more than a 100-fold change in concentration of unlabeled AII was required to compete from 90% specific binding to 10% specific binding suggests the presence of more than one receptor binding affinity site. This was expected since the human cloned AT1 receptor preparation used in this assay possesses both high and low affinity AII binding sites. Therefore, the assay of the invention can also differentiate between the binding of a ligand to a single receptor site model or a multiple receptor site model.

By comparison, all twelve concentrations (from 1 nM to 300 μM) of substance P were unable to displace the binding of 10 nM Flu-AII to 0.02 units of AT1 receptor, resulting in similar decreases in fluorescent intensity as that observed in the absence of any substance P (data not shown), further confirming the specificity of the assay.

While the invention has been described in detail and with reference to specific examples thereof, it will be apparent to one skilled in the art that various changes and modifications can be made therein without departing from the spirit and scope thereof.

What is claimed is:

1. A method for assaying binding between at least one target and at least one probe, said method comprising:

providing at least one target comprising a peptide sequence or a peptide analog sequence;

providing at least one probe consisting essentially of amino acids or amino acid analogs, and at least one fluorophore;

providing a test medium comprising said at least one target and said at least one probe;

binding said at least one target to said at least one probe in said test medium to form a binding complex;

irradiating said test medium with radiation effective to cause said at least one fluorophore to emit fluorescent light; and detecting a quenching effect on fluorescence emitted by said at least one fluorophore resulting from said binding without measuring polarization of said fluorescence, wherein said binding is specific and sufficiently sensitive to detect bound target at a concentration less than $1.5 \times 10^{-11}$ M, and wherein said method is conducted without separating complexes of said at least one target and said at least one probe from free target and free probe prior to said quenching effect detecting, and without providing a signal quenching agent to quench said emitted fluorescence.

2. The method of claim 1, wherein said at least one target is a protein.

3. The method of claim 1, wherein said at least one probe consists of said at least one fluorophore and said amino acids.

4. The method of claim 1, wherein said method is sufficiently sensitive to detect bound target at a concentration of $1.0 \times 10^{-11}$ M or less.

5. The method of claim 1, wherein said method is sufficiently sensitive to detect bound target at a concentration of $3.0 \times 10^{-14}$ M to $1.0 \times 10^{-11}$ M.

6. The method of claim 1, wherein a concentration of said complexes is $3.0 \times 10^{-14}$ M to $10 \times 10^{-11}$ M.

7. The method of claim 1, wherein said at least one target comprises at least one transporter protein or enzyme and said at least one probe comprises a ligand.

8. The method of claim 1, wherein said at least one target comprises at least one receptor and said at least one probe comprises a ligand.

9. The method of claim 8, further comprising performing a dissociation binding experiment to determine a dissociation rate constant, defined as a rate of dissociation of said probe from said target over time.

10. The method of claim 8, further comprising titrating said at least one probe against said at least one target, and determining a receptor saturating amount of probe binding to said at least one target as an amount of said at least one probe producing a maximum in said quenching effect.

11. The method of claim 10, wherein an equilibrium dissociation constant is determined.

12. The method of claim 11, wherein a fractional occupancy is determined, said fractional occupancy indicating a fraction of all receptors on said at least one target occupied by said at least one probe.

13. The method of claim 10, wherein at least one additional ligand is added to said test medium, said at least one additional ligand lacking a fluorophore label.

14. The method of claim 13, further comprising determining whether said at least one additional ligand is an agonist, a competitive antagonist or a non-competitive antagonist.

15. The method of claim 13, wherein said at least one additional ligand competes with said at least one probe for said at least one receptor, and said method determines a binding affinity of said at least one additional ligand for said at least one receptor.

16. The method of claim 13, wherein said at least one additional ligand differs from said at least one probe in that said at least one additional ligand lacks said at least one fluorophore.

17. The method of claim 13, wherein said at least one additional ligand is different from said at least one probe.

18. The method of claim 17, wherein a plurality of different ones of said at least one additional ligand are assayed against said at least one target and said at least one probe to screen for ligands having selected binding characteristics.

19. The method of claim 11, further comprising performing a dissociation binding experiment to determine a dissociation rate constant, defined as a rate of dissociation of said probe from said target over time, and then determining the association rate constant.

20. A method for assaying binding between at least one target and at least one probe, said method comprising:

providing at least one target comprising a peptide sequence or a peptide analog sequence, and at least one fluorophore;

providing at least one probe consisting essentially of amino acids or amino acid analogs;

providing a test medium comprising said at least one target and said at least one probe;

binding said at least one target to said at least one probe in said test medium to form a binding complex;

irradiating said test medium with radiation effective to cause said at least one fluorophore to emit fluorescent light; and detecting a quenching effect on fluorescence emitted by said at least one fluorophore resulting from said binding without measuring polarization of said fluorescence, wherein said binding is specific and sufficiently sensitive to detect bound target at a concentration less than $1.5 \times 10^{-11}$ M, and wherein said method is conducted without separating complexes of said at least one target and said at least one probe from fee target and free probe prior to said quenching effect detecting, and without providing a signal quenching agent to quench said emitted fluorescence.

21. The method of claim 1, wherein said binding complex contains only one said fluorophore.

22. The method of claim 20, wherein said binding complex contains only one said fluorophore.

* * * * *

SEQUENCE LISTING

<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      human octapeptide angiotensin II hormone

<400> SEQUENCE: 1

Asp Arg Val Tyr Ile His Pro Phe
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      human octapeptide angiotensin II hormone segment

<400> SEQUENCE: 2

Asp Arg Val Tyr Ile
 1               5

<210> SEQ ID NO 3
<211> LENGTH: 11
<212> TYPE: PRT
<213> ORGANISM: Human

<400> SEQUENCE: 3

Met Leu Gly Phe Phe Gln Gln Pro Lys Pro Arg
 1               5                  10